United States Patent [19]

Cowan

[11] Patent Number: 4,544,767

[45] Date of Patent: Oct. 1, 1985

[54] DIACYLOXYOLEFINS ARE HYDROGENATED IN PRESENCE OF ALKALI AND ALKALINE EARTH METAL SALTS OF CARBOXYLIC ACIDS

[75] Inventor: Kiplin D. Cowan, Bartlesville, Okla.

[73] Assignee: Phillips Petroleum Company, Bartlesville, Okla.

[21] Appl. No.: 174,425

[22] Filed: Aug. 1, 1980

[51] Int. Cl.$^4$ ............................................. C07C 67/283
[52] U.S. Cl. ..................................... 560/263; 260/409; 260/410.6; 260/410.9 R; 560/1; 560/8; 560/103; 560/105; 560/112; 560/122; 560/123; 560/124; 560/265; 568/858

[58] Field of Search ............. 260/409, 410.6, 410.9 R; 560/263, 103, 112, 1, 105, 265, 8, 122, 123, 124

[56] References Cited

U.S. PATENT DOCUMENTS 4,117,242 9/1978 Fozzard ............................... 560/263

Primary Examiner—Vivian Garner
Attorney, Agent, or Firm—Howard D. Doescher

[57] ABSTRACT

Hydrogenation of an acyloxyolefin is effected in the presence of at least one of an alkali and an alkaline earth metal salt of a carboxylic acid. In one embodiment, 1,4-diacetoxy-2-butene is converted to 1,4-diacetoxybutane employing potassium acetate.

7 Claims, No Drawings

DIACYLOXYOLEFINS ARE HYDROGENATED IN PRESENCE OF ALKALI AND ALKALINE EARTH METAL SALTS OF CARBOXYLIC ACIDS

A BRIEF DESCRIPTION OF INVENTION

Diacyloxyolefins are hydrogenated in the presence of at least one of an alkali and an alkaline earth metal salt of a carboxylic acid, e.g., 1,4-diacetoxy-2-butene, is converted to 1,4-diacetoxybutane with potassium acetate, thus avoiding considerable hydrogenolysis to butyl acetate.

DETAILED DESCRIPTION

This invention relates to the hydrogenation of a diacyloxyolefin. In one of its aspects, it relates to the conversion of a diacyloxyolefin by hydrogenation to the corresponding diacyloxy saturated hydrocarbon.

In one of its concepts, the invention provides a process for the hydrogenation of a diacyloxyolefin in the presence of at least one of an alkali and alkaline earth metal salt of a carboxylic acid. In another of its concepts, the invention provides a process for converting a diacyloxyolefin to the corresponding diacyloxy saturated hydrocarbon in the presence of at least one of an alkali and an alkaline earth metal salt of a carboxylic acid. In a more specific concept of the invention, it provides a process for the hydrogenation of 1,4-diacetoxy-2-butene to 1,4-diacetoxybutane employing a hydrogenation catalyst and at least one of an alkali or alkaline earth metal salt of a carboxylic acid.

The invention is particularly related to a process for producing alkanediols in which a conjugated diene is first halogenated to a dihaloalkene which then is treated with an alkali metal salt of a carboxylic acid, forming a diacyloxyalkene which is then hydrogenated to the diacyloxyalkane which is then hydrolyzed to the corresponding alkanediol.

INVENTIVE BACKGROUND

Diacetoxyalkenes are intermediates used in making alkanediols which are themselves useful products. One such product, 1,4-butanediol, is a raw material in producing tetrahydrofuran (a known solvent) and a relatively new engineering plastic, polybutylene terephthalate.

Several methods are known to produce 1,4-butanediol. One such method is disclosed in U.S. Pat. No. 4,164,616, issued Aug. 14, 1979, wherein 1,4-butanediol is prepared in a 4-step continuous process by: (1) reacting butadiene and bromine to form 1,4-dibromo-2-butene which is almost instantaneously reacted with potassium acetate to form 1,4-diacetoxy-2-butene; (2) hydrogenating the double bond; (3) hydrolyzing to the corresponding diol; and (4) electrolyzing the alkali metal halide by-product to liberate free bromine and alkali metal hydroxide which are then returned for use in the process. Basically, this invention is an improvement in step 2 of the above-mentioned process.

It is known that various additives when present during the hydrogenation of 1,4-diacetoxy-2-butene enhance the conversion to 1,4-diacetoxybutane. For example, U.S. Pat. No. 4,117,242 discloses the use of monoamines such as triethylamine during the hydrogenation of 1,4-diacetoxy-2-butene to 1,4-diacetoxybutane in the presence of a palladium catalyst. Likewise, U.S. Pat. No. 3,919,294 discloses the use of zinc or vanadium in the presence of a nickel catalyst during the same hydrogenation reaction.

U.S. Pat. No. 3,872,163 discloses a catalyst system comprised of palladium on alumina or charcoal and an alkali metal salt of a carboxylic acid such as potassium acetate. However, the catalyst is employed in an oxidation reaction wherein a conjugated diene such as butadiene is reacted with oxygen and acetic acid to give a mixture of 1,4-diacetoxy-2-butene and 1,2-diacetoxy-3-butene. Hydrogenation of these products with the same catalyst is not mentioned.

The disclosures of the patents mentioned herein are incorporated by this reference to them.

It is an object of this invention to produce a diacyloxy saturated hydrocarbon. It is another object of this invention to provide an improved process for the hydrogenation of a diacyloxyolefin. It is a further object of this invention to convert 1,4-diacetoxy-2-butene to 1,4-diacetoxybutane. It is a further object of the invention to improve the hydrogenation effected thereby to avoid the formation of undue amounts of by-product, e.g., butyl acetate as when 1,4-diacetoxy-2-butene is hydrogenated to produce 1,4-diacetoxybutane.

Other aspects, concepts, objects and the several advantages of the invention are apparent from a study of this disclosure and the appended claims.

According to the present invention, a diacyloxyolefin is converted by hydrogenation in the presence of at least one of an alkali and an alkaline earth metal salt of a carboxylic acid.

ACYLOXYALKENES

The acyloxyalkenes useful in this invention are those compounds represented by the formulas I, II and III:

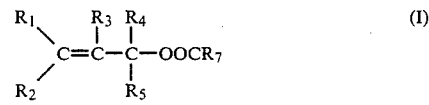

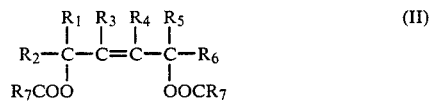

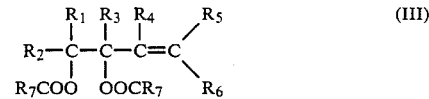

wherein $R_1$ to $R_6$ are individually a hydrogen atom or a hydrocarbon group, more preferably an alkyl group having 1 to 6 carbon atoms; and $R_7$ can be an alkyl, cycloalkyl, or aromatic radical having 1 to 7 carbon atoms. Exemplary of compounds represented by formula I are 2-propenylacetate, 2-butenylacetate, 2-pentenylacetate, 3-pentenylacetate, 2-hexenylacetate, 3-hexenylacetate, 4-hexenylacetate, 2-propenylpropionate, 2-propenylbutyrate, 2-propenylhexanoate, 2-propenylcyclohexylcarboxylate, 2-propenylbenzoate, and the like.

Exemplary of compounds represented by formula II are 1,4-diacetoxy-2-butene, 1,4-dipropionyloxy-2-butene, 1,4-dibutyryloxy-2-butene, 1,4-dibenzoyloxy-2-butene, 1,4-diacetoxy-2-pentene, 1,4-diacetoxy-2-methyl-2-butene, 1,4-diacetoxy-2-hexene, 1,4-diacetoxy-2-octene, and the like.

Exemplary of compounds represented by formula III are 1,2-diacetoxy-3-butene, 1,2-dipropionyloxy-3-butene, 1,2-dibutyryloxy-3-butene, 1,2-dibenzoyloxy-3-butene, 1,2-diacetoxy-3-pentene, 1,2-diacetoxy-2-methyl-3-butene, 1,2-diacetoxy-3-hexene, 1,2-diacetoxy-3-octene, and the like.

The acyloxy- and diacyloxyalkenes described herein are readily prepared by several methods, one of which is to treat a haloalkene or dihaloalkene with an alkali metal salt of a carboxylic acid. Such a method is generally described in U.S. Pat. Nos. 4,164,616; 3,720,704; and 3,723,510. The disclosures of the latter two patents are incorporated herein by this reference to them. Another method describes acyloxyalkenes prepared from alkadienes, carboxylic acids, oxygen, and a catalyst. Such a method is generally described in U.S. Pat. No. 3,872,163.

METAL CARBOXYLATES

Metal carboxylates useful in this invention are those alkali or alkaline earth metal salts of carboxylic acids represented by the formula $$(RCOO)_xM \qquad (IV)$$

wherein x is the valence of M, i.e., 1 or 2, and wherein R can be a hydrogen atom or an alkyl, cycloalkyl, or aromatic radical having 1 to 12 carbon atoms, and M can be any alkali or alkaline earth metal listed in Group IA or IIA of the Periodic Table such as lithium, sodium, potassium, rubidium, cesium, beryllium, magnesium, calcium, etc., with sodium and potassium being preferred. It is also preferred, but not required, that the carboxylate anionic portion of the metal salt be the same as the acyloxy substitution in formulas I, II and III. The amount of metal carboxylate present can be broadly about 1 to about 50 weight percent, preferably about 2 to about 10 weight percent based on the amount of olefin charged. Exemplary of compounds represented by formula IV are: lithium formate, sodium formate, potassium formate, calcium formate, lithium acetate, sodium acetate, potassium acetate, cesium acetate, magnesium acetate, calcium acetate, sodium propionate, potassium butyrate, potassium cyclohexylcarboxylate, potassium benzoate, and the like, and mixtures thereof.

HYDROGENATION CATALYSTS

Hydrogenation catalyst can be any noble metal or nickel catalyst known to be used for such purposes. For example, catalysts based on nickel, palladium, platinum, rhodium, and ruthenium, and the like, are within the scope of this invention. The catalyst can be employed on any suitable support such as alumina, charcoal, etc. It is preferred that the catalyst be heterogeneous to the system, i.e., insoluble in the reaction mixture.

SOLVENTS

Any liquid carboxylic acid or the corresponding anhydride or a mixture of the acid and anhydride can be used as solvents in this invention. It is preferred but not essential that the carboxylic acid solvent possess the same anionic segment as in the metal carboxylate salt or acyloxyalkene employed herein. It is industrially advantageous to use a lower aliphatic carboxylic acid such as acetic acid, propionic acid or butyric acid, etc. Acetic acid is particularly preferred. Other solvents such as methyl alcohol, tetrahydrofuran and dioxane can also be employed provided they are capable of dissolving the acyloxyalkene and metal carboxylate salts employed herein.

REACTION CONDITIONS

The temperature ranges used herein are those usually employed during most hydrogenation reactions. Generally this will be from about 25° C. to 100° C., preferably 25° C. to 75° C. It is most preferred to conduct the reaction as near to ambient room temperature as possible to prevent any influence by temperature on undesired cleavage reactions. The reaction is independent of pressure other than that needed to maintain hydrogen pressure. However, pressures from 0 to 1000 psig are believed to be within the scope of this invention. Usually from 10 to 100 psig $H_2$ is preferred.

The following examples serve to illustrate the invention.

EXAMPLE I

Control Run

This example is a control illustrating product distribution when 1,4-diacetoxy-2-butene is hydrogenated to 1,4-diacetoxybutane in the absence of the inventive compounds, alkali or alkaline earth metal carboxylates. A solution comprised of 8.7 grams of 1,4-diacetoxy-2-butene (99 percent pure) and 80 grams of acetic acid containing about 10 weight percent acetic anhydride was added to a 300 milliliter stainless steel autoclave along with 0.4 gram of a hydrogenation catalyst, 5 weight percent palladium on alumina. The autoclave was sealed, flushed with hydrogen several times, then hydrogen pressured to 30 psig and the stirrer started. The hydrogenation was carried out at ambient room temperature until the hydrogen uptake ceased (about 3.5 hours). The reactor was vented and the reaction mixture filtered. The filtrate was analyzed by GLC using a Hewlett Packard 5750 chromatograph using an 182 cm (6 ft.)×0.635 cm (0.25 in.) glass column of 10 weight percent Carbowax 20M on Teflon and a temperature program of 120° C. (2 min.), 30° C./min. to 220° C., hold at 220° C., 2 min. Analysis indicated the following distribution:

| Wt. % | |
|---|---|
| — | 1,4-Diacetoxy-2-butene (DABE) |
| 5.05 | 1,4-Diacetoxybutane (DABA) |
| 0.70 | Acetic Anhydride ($Ac_2O$) |
| 91.17 | Acetic Acid (AcOH) |
| 1.59 | Butyl Acetate (BA) |

The % area ratio of DABA/BA is estimated at 73.7/26.3 which shows that a significant amount of hydrogenolysis occurs giving non-recyclable butyl acetate. The molar ratio of DABA/BA is estimated as 66.7/33.3. Molar ratio is determined by multiplying the % area by a response factor (1.07 for DABA and 1.00 for BA), changing the adjusted % area to grams and converting to moles. For example:

$$\frac{DABA}{BS} = \frac{73.7}{26.3} \times \frac{1.07}{1.00} =$$

$$= \frac{0.458 \text{ moles}}{0.228 \text{ moles}} = \frac{66.7}{33.3}$$

EXAMPLE II

Invention Run

This example is the invention illustrating that when 1,4-diacetoxy-2-butene is hydrogenated to 1,4-diacetoxybutane in the presence of potassium acetate very little hydrogenolysis to butyl acetate occurs, giving an almost quantitative yield of 1,4-diacetoxybutane. The procedure described in Example I was repeated except potassium acetate was added to the hydrogenation mixture before hydrogenation.

Discussion

The results which are listed in Table I indicate the presence of potassium acetate increases the yield of diacetoxybutane and suppresses hydrogenolysis to butyl acetate. In addition, the hydrogenation reaction is complete in 40 minutes whereas without potassium acetate the hydrogenation required about 3.5 hours to complete.

TABLE I

Effects of Potassium Acetate on the
Hydrogenation of 1,4-Diacetoxy-2-butene
5 Wt. % Pd/Alumina
Temp. 25° C.; Press. 30 psig $H_2$

| Wt. % Potassium Acetate Used[a] | Analysis by GLC | |
|---|---|---|
| | % Area Ratio of DABA/BA | Molar Ratio of DABA/BA |
| 0 (Control Example I) | 73.7/26.3 | 66.7/33.3 |
| 2.2 | 98.9/1.1 | 98.4/1.6 |
| 4.6 | 99.4/0.6 | 99.5/0.5 |
| 13.7 | 98.8/1.2 | 98.3/1.7 |
| 57.3 | 98.6/1.4 | 98.0/2.0 |

[a]Based on weight of 1,4-diacetoxy-2-butene charged.

EXAMPLE III

Invention Run

This example is the invention illustrating that sodium acetate works equally well as potassium acetate in suppressing hydrogenolysis during the hydrogenation of 1,4-diacetoxy-2-butene to 1,4-diacetoxybutane. The procedure described in Example I was again repeated except various amounts of sodium acetate were added to the mixture before hydrogenation.

Discussion

The results shown in Table II indicate higher yields of 1,4-diacetoxybutane than when no sodium acetate is present during hydrogenation. Again, the hydrogenation reaction was complete in about 40 minutes whereas without sodium acetate the hydrogenation required about 3.5 hours to complete.

TABLE II

Effects of Sodium Acetate on the
Hydrogenation of 1,4-Diacetoxy-2-butene
5 wt. % Pd/Alumina
Temp. 25° C.; Press. 30 psig $H_2$

| Wt. % Sodium Acetate Used[a] | Analysis by GLC | |
|---|---|---|
| | % Area Ratio of DABA/BA | Molar Ratio of DABA/BA |
| 0 (Control - Example I) | 73.7/26.3 | 66.7/33.3 |
| 1.6 | 98.3/1.7 | 97.6/2.4 |
| 3.2 | 98.7/1.3 | 98.1/1.9 |
| 6.4 | 98.2/1.8 | 97.5/2.5 |
| 19.2 | 98.2/1.8 | 97.5/2.5 |

[a]Based on weight of 1,4-diacetoxy-2-butene charged.

EXAMPLE IV

Invention Run

This example is the invention illustrating that carboxylates other than acetates are effective in suppressing hydrogenolysis. The procedure described in Example I was again repeated using sodium formate and sodium benzoate as additives.

Discussion

The results listed in Table III show both materials are effective in suppressing hydrogenolysis although with sodium formate the effect is not as great at about the 2 weight percent level as with sodium benzoate and other alkali metal carboxylates at the same concentration.

TABLE III

Effects of Sodium Formate and Sodium Benzoate
on the Hydrogenation of 1,4-Diacetoxy-2-butene
5 wt. % Pd/Alumina
Temp. 25° C.; Press. 30 psig $H_2$

| Alkali Metal Carboxylate | | Analysis by GLC | |
|---|---|---|---|
| Ingredient | Wt. % Used[a] | % Area Ratio of DABA/BA | Molar Ratio of DABA/BA |
| Sodium Formate | 3.3 | 88/12 | 84.0/16.0 |
| Sodium Formate | 13.7 | 100/0 | 100/0 |
| Sodium Benzoate | 3.3 | 98.4/1.6 | 97.8/2.2 |

[a]Based on the weight of 1,4-diacetoxy-2-butene charged.

SUMMARY

In summary, the results herein disclose that during the hydrogenation of 1,4-diacetoxy-2-butene to 1,4-diacetoxybutane, undesirable hydrogenolysis to give butyl acetate can be suppressed which in turn results in higher yields of the desired hydrogenation product 1,4-diacetoxybutane when an alkali metal carboxylate such as sodium or potassium acetate is present during the hydrogenation. In addition, less reaction time is required to complete the hydrogenation when the said metal carboxylates are present during the hydrogenation.

Reasonable variation and modification are possible within the scope of the foregoing disclosure and the appended claims to the invention, the essence of which is that in the hydrogenation of a diacyloxyolefin to the corresponding diacyloxy saturated hydrocarbon, the presence of at least one of an alkali and an alkaline earth metal salt of a carboxylic acid will suppress the formation of undesirable by-products.

That which is claimed is:

1. The hydrogenation of an acyloxyolefin in the presence of about 1–50 wt.% based on the amount of olefin present, of at least one of an alkali and an alkaline earth metal salt of a carboxylic acid.

2. The process according to claim 1 wherein the hydrogenation is effected in the presence of a catalyst and hydrogen.

3. A process according to claim 2 wherein the acyloxyalkene is a compound represented by the formula as follows:

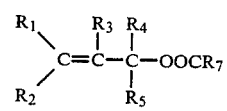

-continued

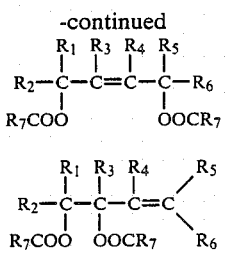

wherein $R_1$ to $R_6$ are individually selected from a hydrogen atom and a hydrocarbon group; and $R_7$ can be an alkyl cycloalkyl, or aromatic radical having 1 to 7 carbon atoms.

4. A process according to claim 3 wherein the acyloxyalkene is at least one selected from the following: 2-propenylacetate, 2-butenylacetate, 2-pentenylacetate, 3-pentenylacetate, 2-hexenylacetate, 3-hexenylacetate, 4-hexenylacetate, 2-propenylpropionate, 2-propenylbutyrate, 2-propenylhexanoate, 2-propenylcyclohexylcarboxylate, 2-propenylbenzoate, 1,4-diacetoxy-2-butene, 1,4-dipropionyloxy-2-butene, 1,4-dibutyryloxy-2-butene, 1,4-dibenzoyloxy-2-butene, 1,4-diacetoxy-2-pentene, 1,4-diacetoxy-2-methyl-2-butene, 1,4-diacetoxy-2-hexene, 1,4-diacetoxy-2-octene, 1,2-diacetoxy-3-butene, 1,2-dipropionyloxy-3-butene, 1,2-dibutyryloxy-3-butene, 1,2-dibenzoyloxy-3-butene, 1,2-diacetoxy-3-pentene, 1,2-diacetoxy-2-methyl-3-butene, 1,2-diacetoxy-3-hexene, and 1,2-diacetoxy-3-octene.

5. A process according to claim 1 wherein 1,4-diacetoxy-2-butene is hydrogenated to 1,4-diacetoxybutane.

6. A process according to claim 1 wherein 1,4-diacetoxy-2-butene is hydrogenated to 1,4-diacetoxybutane in the presence of at least one of an alkali and an alkaline earth metal salt of a carboxylic acid represented by the formula

wherein x is the valence of M, i.e., 1 or 2, and wherein R is a hydrogen atom or an alkyl, cycloalkyl, or aromatic radical having 1 to 12 carbon atoms; and M is at least one metal selected from the group consisting of alkali and alkaline earth metals as listed in Group IA and IIA of the Periodic Table.

7. A process according to claim 1 wherein the acyloxyalkene is converted to the corresponding acyloxysaturated hydrocarbon and wherein the metal salt is one selected from the following: lithium formate, sodium formate, potassium formate, calcium formate, lithium acetate, sodium acetate, potassium acetate, cesium acetate, magnesium acetate, calcium acetate, sodium propionate, potassium butyrate, potassium cyclohexylcarboxylate and potassium benzoate.

* * * * *